United States Patent [19]
Palmenberg et al.

[11] Patent Number: 5,912,167
[45] Date of Patent: Jun. 15, 1999

[54] AUTOCATALYTIC CLEAVAGE SITE AND USE THEREOF IN A PROTEIN EXPRESSION VECTOR

[75] Inventors: Ann C. Palmenberg, Madison, Wis.; Michael A. Hoffman, Shaker Heights, Ohio; Harry Hahn; Lee R. Martin, both of Madison, Wis.

[73] Assignee: Wisconsin Alumni Research Foundation, Madison, Wis.

[21] Appl. No.: 08/468,790

[22] Filed: Jun. 6, 1995

[51] Int. Cl.$^6$ .............................. C12N 15/09; C12N 7/00; C12N 15/00

[52] U.S. Cl. .................... 435/320.1; 536/23.1; 536/23.7; 536/23.72

[58] Field of Search ........................ 435/320.1; 536/23.1, 536/23.7, 23.72

[56] References Cited

U.S. PATENT DOCUMENTS

| | | | |
|---|---|---|---|
| 5,149,783 | 9/1992 | Sommergruber et al. | 530/326 |
| 5,162,601 | 11/1992 | Slightom et al. | 435/320.1 |
| 5,229,111 | 7/1993 | Palmenberg et al. | 424/89 |
| 5,491,076 | 2/1996 | Carrington et al. | 435/70.1 |

FOREIGN PATENT DOCUMENTS

WO 95/17514   6/1995   United Kingdom.

OTHER PUBLICATIONS

Ryan et al. "Foot–and–mouth disease virus 2A oligopeptide mediated cleavage of an artificial polyprotein." EMBO J 13(4):928–933, Feb. 15, 1994.

Palmenberg et al. "Proteolytic processing of cardioviral P2 region: Primary 2A/2B cleavage in clone–derived precursors" Virology 190(2):754–762, Oct. 1, 1992.

Altmeyer, R., et al., "Attenuated Mengo virus as a vector for immunogenic human immunodeficiency virus type 1 glycoprotein 120," *Proc. Natl. Acad. Sci. USA* 91:9755–9779, 1994.

Palmenberg, A.C., "Proteolytic Processing of Picornaviral Polyprotein," *Annu. Rev. Microbiol.* 44:603–23, 1990.

Palmenberg, A.C., et al., "Proteolytic Processing of the Cardioviral P2 Region: Primary 2A/2B Cleavage in Clone–Derived Precursors," *Virology* 190:754–762, 1992.

Palmenberg, A.C., et al., "Cardioviral poly(C) tracts and viral pathogenesis," *Arch. Virol.* 9:67–77, 1994.

Ryan, M.D., et al., "Foot–and–mouth disease virus 2A oligopeptide mediated cleavage of an artificial polyprotein," *EMBO J.* (4):928–933 (vol. unknown), 1994.

Martin, L.R., et al., Abstract, "Molecular Biology of Poly-(C)–mediated Pathogenesis in Mengo virus," American Society for Virology, 12th Annual Meeting, Jul. 10–14, 1993.

Palmenberg, A.C., et al. "Immune Response to Cardiovirus Vaccine Vectors," Keystone Meeting Abstract, Jan. 20, 1995.

Martin, L. R., et al., "Molecular Biology of Poly(C)–mediated Pathogenesis in Mengo virus," "Scientific Program and Abstracts" for the 12th Annual Meeting of the American Society for Virology, Davis, CA, Jul. 10–14, 1993.

Martin, L. R., et al., "Molecular Biology and Vaccine Potential of Cardioviruses with Genetically–Engineered Poly(C) Tracts," Abstracts Book for the IXth International Congress of Virology, Glasgow, Scotland, Aug. 8–13, 1993.

Martin, L. R., et al., "Mengo Virus Virulence: Pseudoknots and Poly(C)," "Scientific Program and Abstracts" for the 13th Annual Meeting of the American Society for Virology, Madison, WI, Jul. 9–13, 1994.

Martin, L. R., et al., "Poly(C)–mediated Virulence & Mengo Virus: cis–& trans–acting Factors," "Scientific Program and Abstracts" for the 14th Annual Meeting of the American Society for Virology, Austin, TX, Jul. 8–12, 1995.

Neal, Z. C., "Picornavirus–Specific CD4$^+$ T Lymphocytes Possessing Cytolytic Activity Confer Protection in the Absence of Prophylactic Antibodies," *J. Virol.* 69(8):4914–4923, 1995.

*Primary Examiner*—Robert A. Wax
*Assistant Examiner*—Bradley S. Mayhew
*Attorney, Agent, or Firm*—Quarles & Brady LLP

[57] ABSTRACT

A nucleic acid construct comprising at least two copies of a nucleic acid sequence encoding an autocatalytic peptide cleavage site is disclosed. This site preferably comprises the amino acid sequence DX(D,E)XNPGP. A method of exposing an animal to an antigenic amino acid sequence is also disclosed.

9 Claims, 6 Drawing Sheets

| | | Δnt | Δaa |
|---|---|---|---|
| EMCR | glyrifnahyagYfadlLihDIEtNPGPfmf | | |
| Δ-13 | pw............adlLihDIEtNPGPfmf | 3744-3926 | 972-1032 |
| Δ-16 | glyr.......gYfadlLihDIEtNPGPfmf | 3897-3917 | 1022-1028 |
| "Δ-17" | glyr......aggfadlLihDIEtNPGPfmf | 3897-3914 | 1022-1027 |
| Δ-19 | glyr....hyagYfadlLihDIEtNPGPfmf | 3897-3908 | 1022-1025 |
| Δ-21 | glyr..nahyagYfadlLihDIEtNPGPfmf | 3897-3902 | 1022-1023 |

FIG. 1

Summary of activities of DIETNPGP mutants

| D | I | E | T | N | P | G | P |
|---|---|---|---|---|---|---|---|
| n (20) | v (90) | d (80) | a (100) | k (30) | l (10) | v (10) | r (10) |
| h (10) | f (10) | | | | q (10) | a (10) | l (30) |
| | | | | | r (10) | e (10) | |
| | | | | | | | w (10) |

Single amino acid mutations of the wild type sequence, given on top, are listed with percent activity relative to wild type in parentheses (rounded to the nearest 10 percent)

FIG. 2

Replacement of the second mengovirus primary cleavage sequence with the EMCV primary cleavage sequence from pM2A2B-M'M' .... 2A | 2B | MCS | 2A | 1° | 2B ....
(SunI) (PmeI)

PCR product encoding EMCV bases 3891 - 3974
EMCV 2A | 2B
(SunI) (PmeI)

2A | 2B | MCS | EMCV 2A | 2B
3716 BstEII — SunI — PmeI — 4136 AflII pM.2A2B-M'E'

Transfer of the BstEII-AflII fragments from pM.2A2B-M'M' and pM.2A2B-M'E' into the same sites of pMC₀

This creates pMC₀M'M' and pMC₀M'E'

FIG. 3C

AUTOCATALYTIC CLEAVAGE SITE AND USE THEREOF IN A PROTEIN EXPRESSION VECTOR

FIELD OF THE INVENTION

The present invention relates in general to the field of recombinant gene expression In particular, the present invention relates to a vector containing at least two copies of a viral autocatalytic cleavage site that is useful for expression of recombinant protein molecules

BACKGROUND OF THE INVENTION

Picornaviruses

Picornaviruses are positive-strand RNA viruses that contain a long open reading frame encoding a polyprotein. Cardioviruses and aphthoviruses are two genera of the picornavirus family. The 5'-end untranslated sequences for these genera are typically 750 to 1,300 nucleotides in length. Some strains of cardioviruses and aphthoviruses have a homopolymeric non-coding poly(C) tract which is located about 150 to 330 bases from the 5'-end of the RNA strand.

The length of the poly(C) tract in cardioviruses and aphthoviruses is usually between 60 to 200 bases and the tract may include discontinuities, such as the insertion of a U residue within the stretch of poly(C).

Both the length of the poly(C) tract and the particular discontinuities are characteristics of a particular strain of cardiovirus or aphthovirus. Examples of poly(C) tract-containing cardioviruses are Mengo viruses, EMCV (encephalomyocarditis virus), ME (Maus Elberfeld), Columbia SK, and MM. Foot and mouth disease virus (FMDV) is an example of an aphthovirus containing a poly(C) tract.

Primary Cleavage in Cardioviruses and Aphthoviruses

Mature viral cardioviral and aphthoviral proteins are derived by progressive, post-translational cleavage of the polyprotein that occurs while the peptides are still nascent on ribosomes. (Reviewed by Palmenberg, et al., *Ann. Rev. Microbiol.* 44:603–623, 1990.) To simplify homolog identification, the European Study Group on the Molecular Biology of Picornaviruses (R. R. Rueckert, et al., *J. Virol.* 50:957–959, 1984) adopted a uniform nomenclature system, designated L-4-3-4, in 1983. Accordingly, mature picornaviral proteins and their precursors are subdivided into four groups (L, P1, P2, P3) on the basis of structure, enzymatic function, and position of primary cleavages.

The leader or "L" proteins are present only in cardio- and aphthoviruses. The EMCV and Mengo leaders are about 7 kd in molecular weight. FMD viruses have two nested L peptides (16 kd and 23 kd), which share common carboxyl ends, but have different in-phase translational start sites (A. R. Carroll, et al., *Nucl. Acids Res.* 6:2381–2390, 1984; S. Forss, et al., *Nucl. Acids Res.* 12:6587–6603, 1984; B. H. Robertson, et al., *J. Virol.* 54:651–660, 1985).

The four P1 peptides are the capsid structural proteins, VP1, VP2, VP3, and VP4 (1D, 1B, 1C, and 1A), named in order of descending molecular weight on polyacrylamide gels (EMCV: 30, 28, 25 and 8 kd). Protein VP0 (1AB), the uncleaved precursor of VP4+VP2, can also be detected at trace levels in virions.

The middle portion of the polyprotein yields peptides 2A, 2B, and 2C (EMCV: 16, 17, and 36 kd). FMDV genomes have very small or deleted 2A sequences when compared to the other viruses. The biological roles of the P2 peptides are currently under examination. The 2A and 2B components are discussed below in conjunction with their activities in the initial steps of polyprotein processing.

The P3 peptides, 3A, 3B, 3C, and 3D (EMCV: 10, 2, 22, and 51 kd) are more closely associated with genome replication. Purified preparations of 3D can catalyze elongation of nascent RNA chains in primer-dependent reactions, an activity that identifies this enzyme as the central element of viral polymerase complexes (J. B. Flanegan, et al., *Proc. Natl. Acad. Sci. USA* 74:2677–2680, 1977; J. B. Flanegan, et al., *J. Virol.* 29:352–360, 1979; R. E. Lundquist, et al., *Proc. Natl. Acad. Sci. USA* 71:4774–4777, 1974; T. A. Van Dyke, et al., *J. Virol.* 35:732–740, 1980). Protein 3B is VPg, the peptide attached to the 5'-end of the genome (M. A. Pallansch, et al., *J. Virol.* 35:414–419, 1980). Protein 3C is a viral-specific protease, responsible for many posttranslational cleavage events (A. E. Gorbalenya, et al., *FEBS Lett.* 108:1–5, 1979; A. C. Palmenberg, et al. *J. Virol.* 32:770–778, 1979; Y. V. Svitkin, et al., *FEBS Lett.* 108:6–9, 1979).

The primary cleavage event within viral polyproteins is co-translational, occurring as soon as a ribosome has reached the middle, or P2 region, of the genome. Distinct processing sites and catalytic mechanisms are used by the various genera. The most thoroughly studied reactions are those of the polio 2A protease, which cleaves its nascent polyprotein at the P1–P2 junction.

A high degree of primary amino acid identity intimates that polio 2A shares its functionality with other members of the enterovirus and rhinovirus genera, but the catalytic sequences are not held in common with the aphthoviruses, cardioviruses, or hepatitis-A viruses. Rather, the cardioviruses (and probably aphthoviruses) seem to achieve efficient primary scission through use of a unique self-cleavage mechanism, dependent on an usually reactive tetrapeptide sequence spanning the 2A–2B junction. The required sequence is not present in hepatitis-A.

Two lines of evidence indicate that cardioviral and aphthoviral 2A peptides are not functionally equivalent to those of the rhino and enteroviruses, and that analogous nascent cleavage activity for these isolates is necessarily located elsewhere in their genomes. First, the 2AB region of aphthoviruses is much shorter than in entero- or rhinoviruses, and sequence comparisons strongly suggest that the missing or deleted segment(s) corresponds to peptide 2A (A. R. Carroll, et al., *Nucl. Acids Res.* 12:2461–72, 1984; A. C. Palmenberg, in *The Molecular Biology of Positive Strand RNA Viruses*, ed. D. J. Rolands, B. W. J. Mahy, M. Mayo, pp. 1–15, London: Academic, 1987; B. H. Robertson, et al., *J. Virol.* 54:651–60, 1985; M. D. Ryan, et al., *Virology* 173:35–45, 1989).

The second rational for an alternative mechanism is that nascent cleavage within cardioviral and aphthoviral polyproteins actually occurs at a different site than in rhino and enteroviruses (2A–2B versus P1-2A), and releases a much larger primary precursor (L-P1-2A versus P1) (M. J. Grubman, et al., *Virology* 116:19–30, 1982; D. S. Shih, et al., *J. Virol.* 30:472–80, 1979). Microsequencing has located the primary site of FMDV-A12 at a G-P sequence, 16 amino acids downstream from the 1D-2A junction (Robertson, et al., *J. Virol.* 54:651–660, 1985). All other sequenced cardio- and aphthovirus strains maintain a G-P pair in the equivalent position.

Relocation to the G-P site did little to clarify the primary mechanism used by these viruses. Unlike the rhino and enteroviruses, where 2A sequences are recognizable as those of a proteolytic enzyme, extensive pattern searches of cardio- and aphthovirus 2AB segments failed to detect identifiable catalytic motifs (A. Palmenberg, unpublished data). Even more puzzling, cell-free translation experiments showed that large segments of the 2A and 2B coding regions could be entirely deleted from engineered EMCV and FMDV RNA transcripts without affecting cleavage activity in the remaining expressed peptide. The L, P1, 2C, and P3 regions of the genome are likewise dispensable for cleavage activity in extracts from a wide variety of cells (e.g. rabbit reticulocyte, HeLa, wheat germ, and insect) (M. D. Ryan, et al., supra, 1989; A. Palmenberg, unpublished data).

The logical alternatives, that (a) some ubiquitous host protease was responsible for primary scission, or (b) that a small common portion of cardio- and aphthovirus polyproteins was autonomously catalytic, were putatively resolved by the recent creation and testing of synthetic peptide sequences. By focusing on the (relatively) conserved segment spanning the 2A–2B junction, Peter Pallai (personal communication) and colleagues demonstrated that synthetic tetrapeptides containing the viral Asn-Pro-Gly-Pro sequence (N-P-G-P) were spontaneously cleaved to Asn-Pro and Gly-Pro when incubated only in buffer. Although detailed mechanistic studies are still incomplete, the astonishing simple autocatalytic reaction seems to be carried out most efficiently in slightly basic reaction mixtures (i.e. pH 8.0), as might be expected for an authentic physiological event.

Missing in the art of molecular biology is a method of using the autocatalytic cleavage site found in picornaviruses to usefully express a recombinant peptide or protein.

SUMMARY OF THE INVENTION

The present invention is a gene construct containing at least two copies of a scission cassette useful in expressing an amino acid sequence that is autocatalytically cleaved from an expression vector.

In one embodiment, the present invention is a gene construct comprising at least two copies of a nucleic acid sequence encoding an autocatalytic peptide cleavage site. (We refer to this nucleic acid sequence as a "scission cassette.") The cleavage site comprises the amino acids NPGP (SEQ ID NO:24). Preferably, the encoded amino acid sequence is DX(D,E)XNPGP (SEQ ID NO:12), wherein "X" indicates that any amino acid residue may be chosen and parentheses indicate that all enclosed residues are suitable. In a more preferred version, the cleavage site comprises the amino acids D(V,I)(D,E)XNPGP (SEQ ID NO:15).

Preferably, at least 17 amino acids are encoded by the scission cassette. In a preferable embodiment, the scission cassette encodes X(Y,F,I)XXXXXXXD(V,I)(D,E)XNPGP (SEQ ID NO:13). In another preferable embodiment, the scission cassette encodes X(Y,F,I)XXXX(L,I)XXD(V,I)(D,E)XNPGP (SEQ ID NO:14).

In a preferred embodiment of the present invention, the gene construct is part of a plasmid or viral vector. In a more preferred embodiment of the present invention, the construct is part of a Mengo virus vector, preferably a Mengo virus vector with a shortened poly(C) region. Preferably, this shortened poly(C) region consists of no C residues.

The present invention is also an efficient method of exposing an animal to an antigenic amino acid sequence in a highly immunogenic context. This method comprises creating a construct with at least two autocatalytic peptide cleavage sites with an amino acid encoding sequence placed between the nucleic acid sequences encoding the cleavage sites. This construct is preferably part of a viral vector comprising nucleic acid sequences necessary to express the amino acid sequence. The viral vector is inoculated into an animal. Subsequently, the amino acid sequence is expressed and the mammal is exposed to the antigenic amino acid sequence.

It is an object of the present invention to provide an improved amino acid sequence expression vector.

It is another object of the present invention to Hprovide a method of exposing a mammal to an antigenic substance.

It is another object of the present invention to provide a vaccination method.

Other objects, features, and advantages of the present invention will become apparent after review of the specification, claims and figures.

DESCRIPTION OF THE DRAWINGS

FIG. 1 is a diagram describing five deletion mutations designed to determine the minimum size of a scission cassette necessary for autocatalytic cleavage.

FIG. 2 is a diagram summarizing the activities of autocatalytic site mutations.

FIG. 4B is a listing of the protein sequence.

DESCRIPTION OF THE INVENTION

1. In General

Figure 3A:
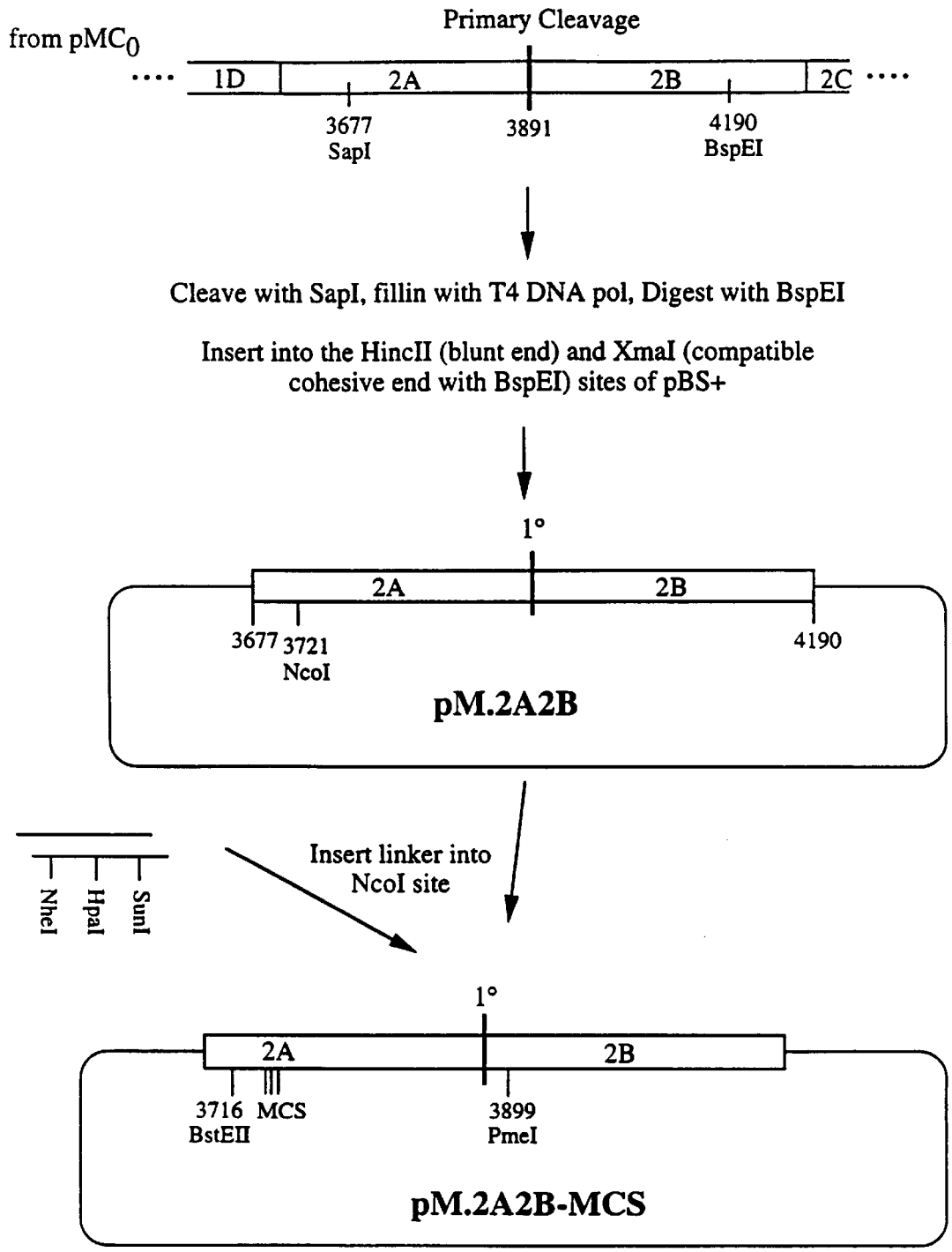
FIG. 3 diagrams the construction of pMC$_0$M'E'.

The present invention is a nucleic acid construct comprising at least two copies of a nucleic acid sequence encoding an autocatalytic peptide cleavage site. This construct will allow one to place a protein coding sequence between the two autocatalytic cleavage sites. When the protein molecule is expressed from the nucleic acid construct, the autocatalytic cleavage sites will automatically cleave the desired foreign protein. If one uses a Mengo virus vector, for example, the vector will be unperturbed and function efficiently.

2. Nucleic Acid Constructs

A "scission cassette" is an RNA or DNA fragment which encodes a protein sequence capable of undergoing monomolecular, autocatalytic self-cleavage in a manner typified by the primary polyprotein cleavage reactions of cardiovirus and aphthoviruses. All natural or experimentally identified scission cassettes encode the exemplar protein sequence: X(Y,F,I)XXXX(L,I)XXD(V,I)(D,E)XNPGP (SEQ ID NO:14). The core sequence NPGP is common to all naturally occurring autocatalytic sequences.

The co-translational scission occurs between the terminal G and P residues of peptides and proteins which contain this sequence. Table 1, below, compares known sequences.

TABLE 1

|  | -16 | -1 | 1 | 7 |  |  | SEQ ID NO: |
|---|---|---|---|---|---|---|---|
| Mengo_M | gyfsdllihDvEtNPG | | Pftfkprq | GB:L22089 | SW: (na) | (3) |
| EMC_B | gyfadllihDiEtNPG | | Pfmakpkk | GB:M22457 | SW:P17593 | (4) |

TABLE 1-continued

| | -16 | -1 | 1 | 7 | | | SEQ ID NO: |
|---|---|---|---|---|---|---|---|
| EMC_R | gyfadllihDiEtNPG | | Pfmfrprk | | GB:M81861 | SW:P03304 | (5) |
| TME_Bean | dyyrqrlihDvEtNPG | | Pvqsvfqp | | GB:M16020 | SW:P08544 | (6) |
| TME_Gd7 | dyykqrlihDvEmNPG | | Pvqsvfqp | | GB:M20301 | SW:P08545 | (7) |
| FMD_O1k | nfdllklagDvEsNPG | | Pfffsdvr | | GB:X00871 | SW:P03305 | (8) |
| Rota_Bov | qidrilisgDiElNPG | | Pnalvkln | | GB:L12390 | SW:P34717 | (9) |
| Rota_Por | qidrilisgDvElNPG | | Pdplirln | | GB:M69115 | SW:P27586 | (10) |
| Consensus | --------- D-E-NPG | | P ------- | | | | (11) |

Referring to Table 1:

Single Letter Amino Codes. Amino acids and protein sequences are commonly designated by one letter codes according to standard nomenclature as set forth by the Nomenclature Committee of the International Union of Biochemistry, 1985, *Eur. J. Biochem.* 150:1–5. In the above table, amino acids common to all sequences of this alignment are indicated in upper case. Amino acids that are not common to all sequences are designated with lower case.

Alignment Information. The alignment shows all known examples of protein sequences within which a scission cassette is functional at the protein level. In some cases, other related viral strains are known to share identical protein sequences (eg: FMDV types A and C share sequence with the indicated type 01k), but in these cases, only one type designate is shown. For the TME, EMC and FMD sequences, protein scission has been experimentally determined to occur between the penultimate glycine (G) and ultimate proline (P) residues of the NPGP tetra-peptide sequence (Palmenberg et al., *Virology* 90:754–762, 1992). According to standard proteolytic conventions these sequence residues are numbered consecutively with plus or minus values according to their position (—COOH direction or $NH_2$ direction respectively) relative to this hydrolyzed peptide bond. The GenBank (GB) database accession numbers of published nucleic acid sequences encoding these proteins segments are given, as are the SwissPro (SW) database accession numbers for the proteins themselves, where available.

Cited Viruses and Protein Location:
Mengo_M: Mengo virus, strain M (medium plaque size), polyprotein primary cleavage sequence
EMC_B: Encephalomyocarditis virus, strain B, polyprotein primary cleavage sequence
EMC_R: Encephalomyocarditis virus, strain Rueckert, polyprotein primary cleavage sequence
TME_Bean: Theilers murine encephalomyelitis virus, strain Bean, polyprotein primary cleavage sequence
TME_Gd7: Theilers murine encephalomyelitis virus, strain GDVII, polyprotein primary cleavage sequence
FMD_O1k: Foot-and-mouth disease virus, strain O1 Kaufbeuren, polyprotein primary cleavage sequence
Rota_Bov: Bovine rotavirus type C, RNA binding protein
Rota_Por: Porcine rotavirus type C, RNA binding protein The autocatalytic peptide cleavage site of the present invention comprises the core sequence NPGP (SEQ ID NO:23). Preferably, the sequence is DX(D,E)XNPGP (SEQ ID NO:12). More preferably, the site comprises the sequence D(V,I)(D,E)XNPGP (SEQ ID NO:15).

In another embodiment, the autocatalytic cleavage site comprises the sequence X(Y,F,I)XXXXXXXD(V,I)(D,E)XNPGP (SEQ ID NO:13). Preferably, the autocatalytic site comprises the amino acid sequence X(Y,F,I)XXXX(L,I)XXD(V,I)D,E)XNPGP (SEQ ID NO:14). Most preferably, the site comprises the sequence XYXXXXLXXDVEXNPGP (SEQ ID NO:16).

It is not necessary that both scission cassettes be identical. In one advantageous embodiment of the present invention, the scission cassettes could be taken from two different naturally occurring picornavirus sequences. The Examples below demonstrate a vector constructed with a scission cassette from both Mengo virus and EMC virus. This is an advantage because the vector will have a lower recombination frequency.

Preferably, the scission cassette is at least 17 amino acids in length with 16 amino acids extending in the minus direction ($NH_2$ direction) and one residue in the plus direction (COOH direction) relative to the cleavage site.

In one version, the scission cassette is a naturally occurring sequence found in picornaviruses, particularly in Mengo viruses. The Examples below demonstrate a Mengo virus with an additional autocatalytic cleavage site and an added nucleic acid sequence encoding a foreign protein added.

To construct the nucleic acid construct of the present invention, one would either obtain a naturally occurring picornavirus sequence or create a nucleic acid sequence encoding the autocatalytic cleavage site synthetically. The nucleic acid construct of the present invention contains at least two of these sites. The site may therefore be part of a naturally occurring molecule or may be artificially created.

Therefore, the Mengo virus described below which contains an additional autocatalytic cleavage site is a nucleic acid construct of the present invention. In the Mengo virus example, one of the sites is naturally occurring and one is added to the viral vector.

If one wishes, more than two cleavage sites may be placed on a vector. This would enable one to create a peptide or protein with several cleavage events.

Preferably, the nucleic acid construct is part of a plasmid or viral vector. Most preferably, the nucleic acid construct is part of a Mengo virus vector with a shortened, preferably deleted, poly(C) region, as described below in the Examples.

Preferably, a polylinker site is placed between the two scission cassettes. One would therefore easily be able to insert a nucleic acid sequence encoding a desired protein or peptide.

If the nucleic acid construct is part of a viral vector, such as Mengo virus, it is an advantage of the present invention that the virus is not unnaturally perturbed after the expression of the foreign-protein. Therefore, one would get more efficient expression of the protein. If one wished to use the viral vector to express the protein in an immunogenic context, for example in a vaccination procedure, it would be important to get a sufficient expression of the antigenic protein or peptide.

In a preferable example of a nucleic acid construct of the present invention, sequences necessary to express the amino acid sequence are contained within the vector.

3. Method of Exposing an Animal to an Antigenic Amino Acid Sequence

The present invention is also a method of exposing an animal, preferably mammal, to an antigenic amino acid sequence. This method requires first creating a construct as described above, wherein the construct is part of a vector that comprises nucleic acid sequences necessary to express the amino acid sequence. A preferred example of such a vector is the Mengo virus vector described herein. One then preferably amplifies the viral vector to obtain a sufficient amount to inject in an animal. The animal is infected with the viral vector and the antigenic amino acid is produced.

Preferably, an immunological response is obtained and the animal is protected against naturally occurring versions of the antigenic amino acid sequence. The immunological response may be measured by measuring the amount of antibody specific for the inserted antigen.

EXAMPLES

A. Required Size of Scission Cassette Within an EMCV Polyprotein Context.

Site-directed deletion mutations were engineered into an EMCV-R cDNA near the region encoding the scission cassette. The purpose of these experiments was to determine the effects of altered protein contexts at different distances from the $NH_2$ side of the scission site (G/P).

FIG. 1 describes these deletion mutations. (SEQ ID NOS:18–23 list the peptide sequences.) The effects (observed protein bands) were measured in an in vitro translation assay in reticulocyte extracts and monitored by autoradiography after polyacrylamide gel fractionation. The five deletions described in FIG. 1 were constructed and tested. The deletions successively perturbed the native viral amino acid sequences at 22, 20, 18, 17 and 14 residues $NH_2$ to the scission site (Δ21, Δ19, Δ17, Δ16, and Δ13, respectively).

Upon translation in reticulocyte extracts, the wild-type sequences gave one band on an analytical gel, as expected in this assay. This wild-type gel profile is indicative of complete and efficient scission at the NPGP site. Deletions Δ16, Δ19 and Δ21 had virtually identical (to wild-type) patterns and mark these residues as unlikely requirements for the scission reaction. Deletion Δ13, however was cleaved inefficiently, and a band of uncleaved precursor was evident on the gel. Deletion Δ17, contains in addition to its deletion sequence, an amino acid substitution (Y to G) at position −15. Scission of this sequence was also inefficient during the in vitro reactions.

We conclude that the preferable size of the cassette is at least 17 amino acids in length: extending 16 residues in the minus direction ($NH_2$ direction) and 1 residue in the plus direction (COOH direction) relative to the cleavage site. For example, the Mengo virus cassette would be GYFSDLLI-HDVETNPGP (SEQ ID NO:17) with cleavage between the G and P. (See Ryan and Drew, EMBO J. 13[4]:928–933, 1994 for a demonstration of a suitable autocatalytic cleavage site with 14 residues culminating in the NPGP sequence.)

Larger cassettes may potentially function more efficiently, but the boundaries determined by this experiment probably describe the most important catalytic requirements of the region. This conclusion is consistent with all published and unpublished data known to us regarding active and inactive cleavage sequences in cardiovirus and aphthovirus sequences.

B. Protein Sequence Requirements for Scission Cassette Activity.

Table 1, above, shows sequence heterogeneity in naturally occurring scission cassette regions. The consensus among all these sequences is an absolutely conserved motif of DXEXNPGP (SEQ ID NO:11), which probably defines, in a general way, the most important elements of the scission cassette. (The designation "X" indicates that any amino acid is suitable.)

To test this hypothesis and to look for other variability, we introduced 15 different site-specific mutations into a scission cassette cDNA from EMCV and then tested the resultant mutant proteins in cell-free reticulocyte translation assays for their ability to undergo cleavage. FIG. 2 describes these mutations and summarizes their activity.

The reactions (radiolabeled protein products) were monitored by autoradiography after fractionation on polyacrylamide gels.

Most mutations were very effective at inhibiting the protein scission. Exceptions were I to V at −6 (a natural sequence variation in the TME viruses), E to D at −5, and T to A at −4, which showed between 80–100% of the cleavage extent as wild type sequences in these assays.

Therefore, the reactive core of any scission cassette must contain the sequence DX(D,E)XNPGP (SEQ ID NO:12). (Amino acid residues within parentheses are alternative suitable residues). This specific motif is extremely rare within the universe of sequenced proteins and does not occur randomly with any significantly observable frequency.

A broader definition of the required scission cassette sequence, which more completely defines all extant mutational and naturally occurring active sequence information is: X(F,Y,I)XXXX(L,I)XX(D,E)(V,I)(D,E)XNPGP (SEQ ID NO:14).

Within this broader context, it must be emphasized that not all of these additional "required" residues have been exhaustively tested by mutagenesis, and it is probably that other related sequences might also prove active.

C. Description of Cardioviral cDNAs

Plasmid $pMC_0$ is similar to other cDNA constructions which contain infectious Mengo viral sequences, such as pMwt, $pMC_{24}$, $pMC_{12}$ and $pMC_8$ (Duke and Palmenberg, J. Virology 63:1822–1826, 1989, incorporated herein by reference). For all of these plasmids, the Mengo-derived cDNA segments are oriented within their vectors (pBS Bluescribe M13+) such that reactions with T7 RNA polymerase produces positivesense, full-length genomic RNA transcripts containing just 2 nonviral bases (GG) at the 5' end and 7 nonviral bases (BamHI site) linked to the 3' viral poly($A_{23}$) (Duke and Palmenberg, J. Virology 63:18221826, 1989; Osorio, Hubbard, Soike, Girard, van der Werf, and Palmenberg, 1995, Vaccine, in press).

However, $pMC_0$ and the infectious virus derived from it ($vMC_0$) are distinguished from the other described strains because the 5' noncoding homopolymeric viral polycytidine tract (poly(C)) which normally occupies viral bases 148–208 (GenEmbl sequence accession number: L22089), have been precisely deleted in the $pMC_0$ construction. The $vMC_0$ virus strain, therefore has a poly(C) tract of length zero.

D. Attenuation of $vMC_0$ Virus

The median lethal dose 50% ($LD_{50}$) for $vMC_0$ virus in mice upon intracerebral inoculation is higher ($>2.0\times10^9$ plaque forming units (PFU)) than for any other genetically engineered Mengo virus with a shortened poly(C) tract. $vMC_0$ has been tested in two strains of mice: outbred Swiss ICR and BALB/c, and is the most highly attenuated (highest $LD_{50}$) of any tested shortened poly(C) Mengo virus. Table 2 describes these results.

TABLE 2

Median Lethal Dose 50% (LD50s) in Mice

| virus | poly(C) tract | LD50 (PFU) |
|---|---|---|
| *Swiss ICR mice* | | |
| vMwt | $C_{44}UC_{10}$ | 9 |
| $vMC_{37}$ | $C_{26}UC_{10}$ | $7.0 \times 10^2$ |
| $vMC_{30}$ | $C_{19}UC_{10}$ | $6.0 \times 10^4$ |
| $vMC_{24}$ | $C_{13}UC_{10}$ | $8.0 \times 10^6$ |
| $vMC_8$ | $C_8$ | $\sim 1.0 \times 10^7$ |
| $vMC_0$ | $C_0$ | $>2.0 \times 10^9$ |
| *BALB/c mice* | | |
| vMwt | $C_{44}UC_{10}$ | $1.3 \times 10^4$ |
| $vMC_{43}$ | $C_{32}UC_{10}$ | $8.0 \times 10^4$ |
| $vMC_{37}$ | $C_{26}UC_{10}$ | $1.3 \times 10^5$ |
| $vMC_{24}$ | $C_{13}UC_{10}$ | $>3.0 \times 10^8$ |
| $vMC_0$ | $C_0$ | $>2.0 \times 10^9$ |

Referring to Table 2, comparative LD50s among select poly(C) tract mutant viruses in Swiss and BALB/c mice are tabulated. Four-to-six week old female littermates were inoculated intracerebrally with 0.02 ml or virus in PBSA. At two weeks post-inoculation, the number of alive and dead mice were used to calculate LD50 values by the method of Reed and Muench (*Am. J. Hygiene* 27[3]:493–497).

E. Construction of $pMC_0M'M'$ and $pMC_0M'E'$.

FIG. 3 describes the construction of $pMC_0M'M'$ and $pMC_0M'E'$. A DNA fragment containing Mengo virus bases 3677 to 4190 which encodes the primary cleavage sequence and parts of viral proteins 2A and 2B was inserted into the vector pBS+ (Stratagene). To do this, plasmid $pMC_0$ was digested with SapI, the overhang filled in with T4 DNA polymerase and then digested with BspEI. The 513 bp fragment was then inserted into the HincII (blunt) and XmaI (compatible cohesive end with BspEI) sites of pBS+. The resultant subclone, pM.2A2B, was then linearized with NcoI (Mengo base 3721) and a 21 bp linker encoding NheI, HpaI and SunI restriction sites was inserted into the NcoI site.

This linearization and linker insertion created plasmid pM.2A2B-MCS (Multiple Cloning Site). pM.2A2B-MCS was then digested with BstEII, which cuts at Mengo base 3716, and the overhang filled in with T4 DNA polymerase, then digested with PmeI, which cuts at viral base 3899. The 204 base pair BstEII-PmeI fragment (including the linker sequences) was then inserted into the PmeI site of pM.2A2B. In this step the BstEII site is destroyed while the PmeI site remains intact. The 204 bp BstEII-PmeI fragment encodes the scission cassette sequence. Thus, insertion of this sequence into pM.2A2B creates a duplication of the scission cassette sequences. In this case both scission cassettes are encoded by Mengo virus sequences. This construct was called pM.2A2B-M'M'.

Transfer of the BstEII—AflII fragment from pM.2A2B-m'm' into the same sites of $pMC_0$ created a full-length construct containing a Mengo virus scission cassette, followed by the multiple cloning site and then another Mengo virus scission cassette within in a Mengo virus genome context containing a poly(C) tract of length zero. This construction was called $pMC_0M'M'$.

The EMCV-R cDNA segment that was amplified to provide a scission cassette for $pMC_0M'E'$ (described below) was derived from a complete infectious cDNA copy of the EMCV-Rueckert genome, plasmid $vEC_9$ (Hahn and Palmenberg, *J. Virology* 69:2697–2699, 1995). The complete genomic sequence of EMCV-R is available from GenEmbl accession number: M81816.

To replace the second Mengo virus scission cassette sequence with the EMCV scission cassette sequence, EMCV bases 3891 to 3974 were amplified by PCR (polymerase chain reaction) and used to replace a SunI—PmeI fragment from pM.2A2B-M'M'. The resulting plasmid was called pM.2A2B-M'E'.

Transfer of the BstEII—AflII fragment from pM.2A2B-M'E' into the equivalent sites of $pMC_0$ created a full-length construct containing the Mengo virus scission cassette followed by the multiple cloning site and then an EMCV scission cassette in a Mengo virus genome context containing a poly(C) tract of length zero. This construction was called $pMC_0M'E'$.

F. Examples of Foreign Sequences Inserted and Expressed from Duplicate Scission Cassette Vector.

Foreign sequences can be inserted directly into the multiple cloning site which is between the two primary cleavage sites in the full-length $pMC_0M'M'$ or $pMC_0M'E'$ clones. In an alternative cloning strategy, foreign sequences could be inserted into the multiple cloning site within pM.2A2B-M'M' or pM.2A2B-M'E', then subsequently transferred into $PMC_0$.

Figure 4:
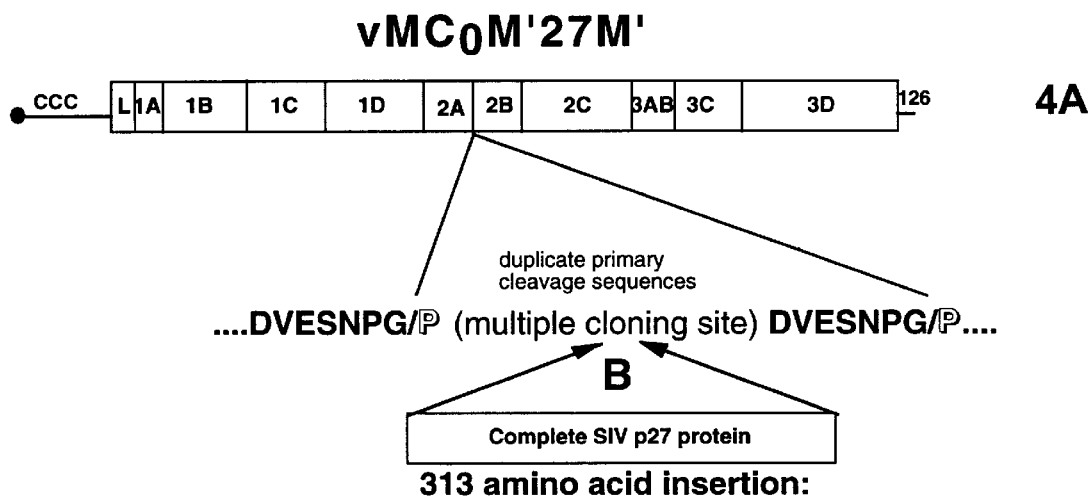
FIG. 4 is a diagram of the Mengo virus vMC$_0$M'27M' genome showing the insertion of SIV p27 protein-encoding sequence into the multiple cloning site between two Mengo scission cassettes.

For example, sequences encoding the simian immunodeficiency virus (SIV) nucleocapsid protein (p27) were inserted into the multiple cloning sites of both $pMC_0M'M'$ and $pMC_0M'E'$. The SIV p27 sequence was amplified by PCR using synthetic primers which encoded the NheI and SunI sites of the duplication scission cassette vectors' multiple cloning site. The resultant PCR product was first ligated (subcloned) into the SmaI site of pBS-SK+ (Stratagene) for easier manipulation and sequence verification. The NheI-SunI fragment containing the p27 sequence from this subclone was then excised from the plasmid, and inserted into NheI/SunI digested $pMC_0M'M'$ or $pMC_0M'E'$ DNA. This procedure created two new plasmids, $pMC_0M'27M'$ and $pMC_0M'27E'$, which contained the p27 sequence inserted (within the viral polyprotein reading frame) between the two viral scission cassette sequences (see FIG. 4).

FIG. 4A is a diagram of the Mengo $vMC_0M'27M'$ genome, showing insertion of SIV p27 protein-encoding sequence into the multiple cloning site between two Mengo scission cassettes. The amino acid sequence of the autocatalytic site is listed at SEQ ID NO:1.

FIG. 4B lists the protein sequence. Referring to FIG. 4B, the underlying sequences are part of the duplicated scission cassettes. The shadowed sequences are derived from translation of the vector's multiple cloning site. SIV sequences are between these multiple cloning site sequences. The total length of the heterologous insertion is 313 amino acids relative to viral protein expressed from $pMC_0$ plasmid. The amino acid sequence in FIG. 4B is listed at SEQ ID NO:2.

As a test of whether the p27 sequences were correctly inserted, and to verify that both scission cassettes would cleave properly within this new context (inserted foreign gene), RNA transcripts from $pMC_0M'27M'$ and $pMC_0M'27E'$ were translated in rabbit reticulocyte extracts, and the protein products (radiolabeled) monitored by autoradiography after fractionation by gel electrophoresis. A unique band was produced from each of these constructs, which was not produced from the parental sequences. The 34 kDa protein and the 29 kDa protein observed were exactly the sizes expected for the inserted p27 protein, if expressed and properly cleaved from the viral polyprotein. Thus, we conclude that both scission cassettes functioned properly and efficiently within each of these sequences.

Addition of purified viral $3C^{pro}$ (protease) enzyme to duplicate samples of these translation products, also showed the expected proteolytic processing of the L-P1-2A viral capsid precursor protein, but did not affect the putative p27 bands in the respective samples. Again, this result is expected if p27 were expressed correctly and excised from the viral polyprotein in a co-translational manner (e.g. did not require exogenous 3C addition for release from the polyprotein).

G. Immunogenic Expression of Foreign Genes in Mice (in progress).

vMC$_0$M'27M' and vMC$_0$M'27E' virus was amplified in HeLa cell tissue culture, and prepared for injection (intraperitoneal and/or subcutaneous) into Balb/c mice. These procedures are exactly analogous to those described for the delivery of other foreign genes via alternative Mengo vectors into mice (Altmeyer, Escriou, Girard, Palmenberg and van der Werf, *PNAS* 91:9775–9779, 1994, incorporated by reference), except for the strain of virus was injected.

Sera samples will be collected from inoculated animals at 2, 4, 6 and 8 weeks post inoculation and tested for the presence of anti-p27 antibodies by ELISA assays (as described in Altmeyer et al, 1994, supra). We foresee that anti-p27 antibodies will be present in the sample sera.

---

We claim:

1. A nucleic acid construct comprising at least two copies of a nucleic acid sequence encoding an autocatalytic peptide cleavage site, wherein the site comprises the amino acid sequence X(Y,F,I)XXXXXXXD(V,I)(D,E)XNPGP (SEQ ID NO:13) and wherein the construct is a part of a replication competent picornavirus viral sequence and wherein the copies are located at the site of a naturally occurring autocatalytic ceavage site.

2. The construct of claim 1 wherein the nucleic acid sequence encodes X(Y,F,I)XXXX(L,I)XXD(V,I)(D,E) XNPGP (SEQ ID NO:14).

3. The construct of claim 2 wherein the nucleic acid sequence encodes XYXXXXLXXDVEXNPGP (SEQ ID NO:16).

4. The construct of claim 1 wherein a polylinker is between two copies of the nucleic acid sequence encoding the autocatalytic site.

5. The construct of claim 4 wherein a nucleic acid sequence encoding an amino acid sequence is placed between said nucleic acid sequences encoding autocatalytic peptide cleavage sites.

6. The construct of claim 5 wherein the amino acid sequence comprises a polyprotein, wherein the polyprotein comprises heterologous proteins that are separated by the autocatalytic cleavage sites.

7. The construct of claim 1 wherein the vector is a Mengo virus.

8. The construct of claim 7 wherein the Mengo virus has a shortened poly(C) region.

9. The construct of claim 8 wherein the construct has a deleted poly(C) region.

* * * * *

UNITED STATES PATENT AND TRADEMARK OFFICE
CERTIFICATE OF CORRECTION

PATENT NO. : 5,912,167
DATED : June 15, 1999
INVENTOR(S) : Ann C. Palmenberg, et al.

It is certified that error appears in the above-identified patent and that said Letters Patent is hereby corrected as shown below:

Title page, item [56] References Cited

In the Altemeyer, R., et al. reference, "91:9755-9779" should be --91;9775-9779--.

Column 4, Line 13:

"Hprovide" should be --provide--.

Figure 3B:
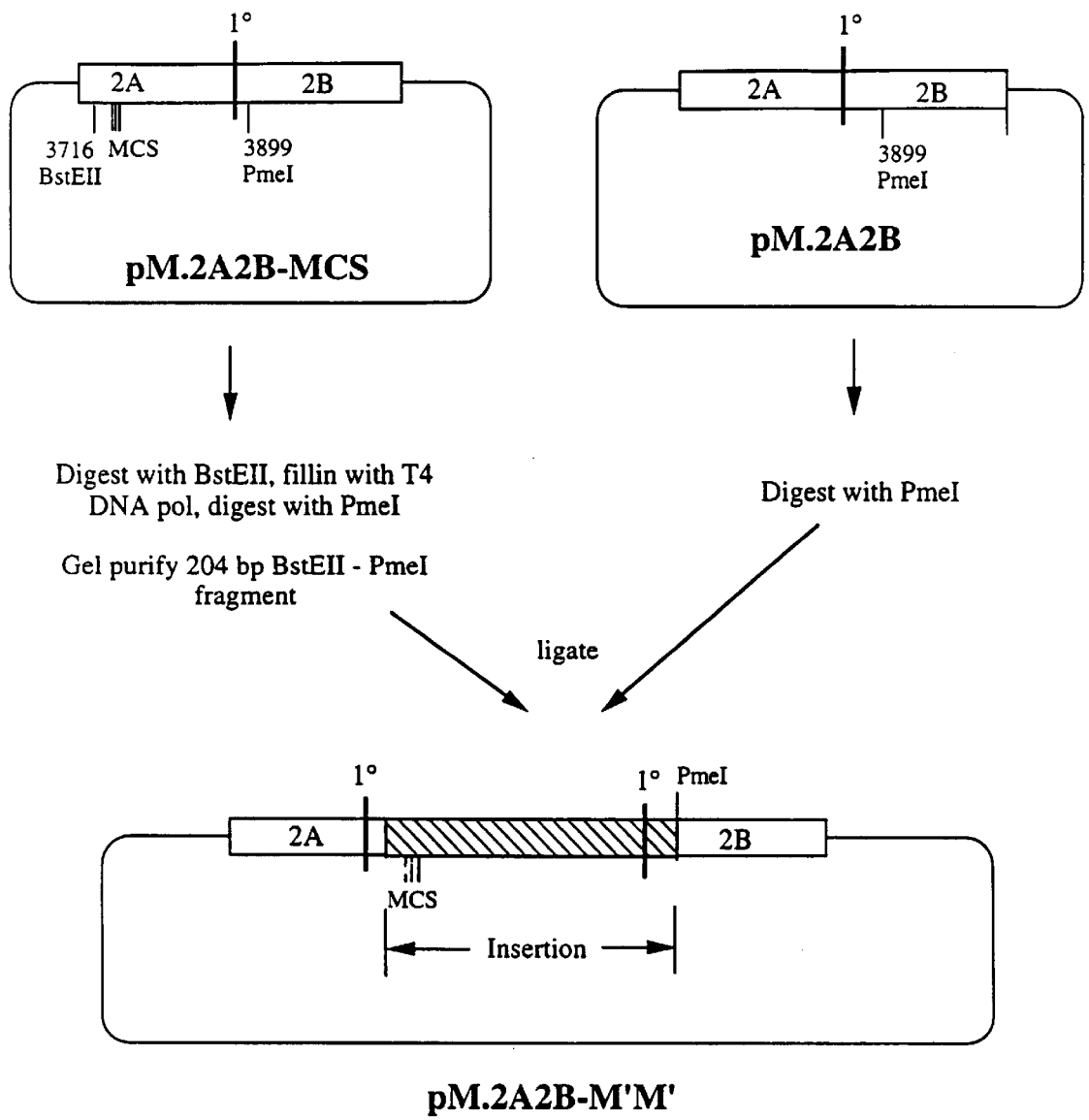

At Column 4, Line 28, please remove "Fig. 3 diagrams" and replace with --Fig. 3A, 3B and 3C diagrams--.

At Column 1

After the title and before the first line of the specification please added the following:

--This invention was made with United States Government support awarded by NIH GRANT # NIH PROJECT #5 R01 AI30566-04. The United States Government has certain rights in this invention.--

UNITED STATES PATENT AND TRADEMARK OFFICE
CERTIFICATE OF CORRECTION

PATENT NO. : 5,912,167
DATED : June 15, 1999
INVENTOR(S) : Ann C. Palmenberg, et al.

It is certified that error appears in the above-identified patent and that said Letters Patent is hereby corrected as shown below:

<u>In the Claims</u>:

In Claim 5, [Claim 4] should read <u>Claim 1</u>.

Signed and Sealed this

Sixth Day of June, 2000

Attest:

Q. TODD DICKINSON

*Attesting Officer*   *Director of Patents and Trademarks*

SEQUENCE LISTING

```
(1) GENERAL INFORMATION:

(iii) NUMBER OF SEQUENCES: 24

(2) INFORMATION FOR SEQ ID NO:1:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:1:

Asp Val Glu Ser Asn Pro Gly Pro
1               5

(2) INFORMATION FOR SEQ ID NO:2:

(i) SEQUENCE CHARACTERISTICS:
          (A) LENGTH: 350 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:2:

Phe Glu Thr His Tyr Ala Gly Tyr Phe Ser Asp Leu Leu Ile His Asp
1               5                   10                  15

Val Glu Thr Asn Pro Gly Pro Phe Thr Phe Val Thr Met Leu Ala Glu
            20                  25                  30

Thr Met Pro Lys Thr Ser Arg Pro Thr Ala Pro Ser Ser Gly Arg Gly
        35                  40                  45

Gly Asn Tyr Pro Val Gln Gln Ile Gly Gly Asn Tyr Val His Leu Pro
    50                  55                  60

Leu Ser Pro Arg Thr Leu Asn Ala Trp Val Lys Leu Ile Glu Glu Lys
65                  70                  75                  80

Lys Phe Gly Ala Glu Val Val Pro Gly Phe Gln Ala Leu Ser Glu Gly
                85                  90                  95

Cys Thr Pro Tyr Asp Ile Asn Gln Met Leu Asn Cys Val Gly Asp His
            100                 105                 110

Gln Ala Ala Met Gln Ile Ile Arg Asp Ile Ile Asn Glu Glu Ala Ala
        115                 120                 125

Asp Trp Asp Leu Gln His Pro Gln Pro Ala Pro Gln Gln Gly Gln Leu
    130                 135                 140

Arg Glu Pro Ser Gly Ser Asp Ile Ala Gly Thr Thr Ser Ser Val Asp
145                 150                 155                 160
```

```
Glu Gln Ile Gln Trp Met Tyr Arg Gln Gln Asn Pro Ile Pro Val Gly
            165                 170                 175
Asn Ile Tyr Arg Arg Trp Ile Gln Leu Gly Leu Gln Lys Cys Val Arg
            180                 185                 190
Met Tyr Asn Pro Thr Asn Ile Leu Asp Val Lys Gln Gly Pro Lys Glu
            195                 200                 205
Pro Phe Gln Ser Tyr Val Asp Arg Phe Tyr Lys Ser Leu Arg Ala Glu
            210                 215                 220
Gln Thr Asp Ala Ala Val Lys Asn Trp Met Thr Gln Thr Leu Leu Ile
225                 230                 235                 240
Gln Asn Ala Asn Pro Asp Cys Lys Leu Val Leu Lys Gly Leu Gly Val
            245                 250                 255
Asn Pro Thr Leu Glu Glu Met Leu Thr Ala Cys Gln Gly Val Gly Gly
            260                 265                 270
Pro Gly Gln Lys Ala Ser Val Arg Met Asp Val Tyr His Lys Arg Ile
            275                 280                 285
Arg Pro Phe Arg Leu Pro Leu Val Gln Lys Glu Trp Arg Thr Cys Glu
            290                 295                 300
Glu Asn Val Phe Gly Leu Tyr His Val Phe Glu Thr His Tyr Ala Gly
305                 310                 315                 320
Tyr Phe Ser Asp Leu Leu Ile His Asp Val Glu Thr Asn Pro Gly Pro
            325                 330                 335
Phe Thr Phe Lys Pro Arg Gln Arg Pro Val Phe Gln Thr Gln
            340                 345                 350

(2) INFORMATION FOR SEQ ID NO:3:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Gly Tyr Phe Ser Asp Leu Leu Ile His Asp Val Glu Thr Asn Pro Gly
1               5                   10                  15
Pro Phe Thr Phe Lys Pro Arg Gln
                20

(2) INFORMATION FOR SEQ ID NO:4:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Gly Tyr Phe Ala Asp Leu Leu Ile His Asp Ile Glu Thr Asn Pro Gly
1               5                   10                  15
Pro Phe Met Ala Lys Pro Lys Lys
                20

(2) INFORMATION FOR SEQ ID NO:5:

(i) SEQUENCE CHARACTERISTICS:
        (A) LENGTH: 24 amino acids
```

(B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Gly Tyr Phe Ala Asp Leu Leu Ile His Asp Ile Glu Thr Asn Pro Gly
1               5                  10                  15

Pro Phe Met Phe Arg Pro Arg Lys
            20

(2) INFORMATION FOR SEQ ID NO:6:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Asp Tyr Tyr Arg Gln Arg Leu Ile His Asp Val Glu Thr Asn Pro Gly
1               5                  10                  15

Pro Val Gln Ser Val Phe Gln Pro
            20

(2) INFORMATION FOR SEQ ID NO:7:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Asp Tyr Tyr Lys Gln Arg Leu Ile His Asp Val Glu Met Asn Pro Gly
1               5                  10                  15

Pro Val Gln Ser Val Phe Gln Pro
            20

(2) INFORMATION FOR SEQ ID NO:8:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Asn Phe Asp Leu Leu Lys Leu Ala Gly Asp Val Glu Ser Asn Pro Gly
1               5                  10                  15

Pro Phe Phe Phe Ser Asp Val Arg
            20

(2) INFORMATION FOR SEQ ID NO:9:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Gln Ile Asp Arg Ile Leu Ile Ser Gly Asp Ile Glu Leu Asn Pro Gly
1               5                   10                  15

Pro Asn Ala Leu Val Lys Leu Asn
            20

(2) INFORMATION FOR SEQ ID NO:10:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Gln Ile Asp Lys Ile Leu Ile Ser Gly Asp Val Glu Leu Asn Pro Gly
1               5                   10                  15

Pro Asp Pro Leu Ile Arg Leu Asn
            20

(2) INFORMATION FOR SEQ ID NO:11:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Asp Xaa Glu Xaa Asn Pro Gly Pro
1               5

(2) INFORMATION FOR SEQ ID NO:12:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /note= "The third residue may be
            either D or E"

(xi) SEQUENCE DESCRIPTION: SEQ ID NO:12:

Asp Xaa Xaa Xaa Asn Pro Gly Pro
1               5

(2) INFORMATION FOR SEQ ID NO:13:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide (B) LOCATION: 1..17
            (D) OTHER INFORMATION: /note= "The second residue may be
                Y,F or I. The eleventh residue may be V or I. The
                twelfth residue may be D or E"

(xi) SEQUENCE DESCRIPTION: SEQ ID NO:13:

Xaa Xaa Xaa Xaa Xaa Xaa Xaa Xaa Xaa Asp Xaa Xaa Xaa Asn Pro Gly
1               5                  10                  15

Pro (2) INFORMATION FOR SEQ ID NO:14:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..17
        (D) OTHER INFORMATION: /note= "The second residue may be
            Y,F or I. The Eleventh residue may be V or I. The
            twelfth residue may be D or E. The seventh residue
            may be L or I."

(xi) SEQUENCE DESCRIPTION: SEQ ID NO:14:

Xaa Xaa Xaa Xaa Xaa Xaa Xaa Xaa Xaa Asp Xaa Xaa Xaa Asn Pro Gly
1               5                  10                  15

Pro (2) INFORMATION FOR SEQ ID NO:15:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /note= "The second residue may be V
            or I. The third residue may be D or E."

(xi) SEQUENCE DESCRIPTION: SEQ ID NO:15:

Asp Xaa Xaa Xaa Asn Pro Gly Pro
1               5

(2) INFORMATION FOR SEQ ID NO:16:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Xaa Tyr Xaa Xaa Xaa Xaa Leu Xaa Xaa Asp Val Glu Xaa Asn Pro Gly
1               5                  10                  15

Pro (2) INFORMATION FOR SEQ ID NO:17:

(i) SEQUENCE CHARACTERISTICS:
    (A) LENGTH: 17 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:17:

```
Gly Tyr Phe Ser Asp Leu Leu Ile His Asp Val Glu Thr Asn Pro Gly
1               5                   10                  15
Pro
```

(2) INFORMATION FOR SEQ ID NO:18:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Gly Leu Tyr Arg Ile Phe Asn Ala His Tyr Ala Gly Tyr Phe Ala Asp
1               5                   10                  15
Leu Leu Ile His Asp Ile Glu Thr Asn Pro Gly Pro Phe Met Phe
            20                  25                  30
```

(2) INFORMATION FOR SEQ ID NO:19:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

```
Pro Trp Ala Asp Leu Leu Ile His Asp Ile Glu Thr Asn Pro Gly Pro
1               5                   10                  15
Phe Met Phe
```

(2) INFORMATION FOR SEQ ID NO:20:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Gly Leu Tyr Arg Gly Tyr Phe Ala Asp Leu Leu Ile His Asp Ile Glu
1               5                   10                  15
Thr Asn Pro Gly Pro Phe Met Phe
            20
```

(2) INFORMATION FOR SEQ ID NO:21:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Gly Leu Tyr Arg Ala Gly Gly Phe Ala Asp Leu Leu Ile His Asp Ile
1               5                   10                  15

Glu Thr Asn Pro Gly Pro Phe Met Phe
            20                  25

(2) INFORMATION FOR SEQ ID NO:22:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Gly Leu Tyr Arg His Tyr Ala Gly Tyr Phe Ala Asp Leu Leu Ile His
1               5                   10                  15

Asp Ile Glu Thr Asn Pro Gly Pro Phe Met Phe
            20                  25

(2) INFORMATION FOR SEQ ID NO:23:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Gly Leu Tyr Arg Asn Ala His Tyr Ala Gly Tyr Phe Ala Asp Leu Leu
1               5                   10                  15

Ile His Asp Ile Glu Thr Asn Pro Gly Pro Phe Met Phe
            20                  25

(2) INFORMATION FOR SEQ ID NO:24:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

Asn Pro Gly Pro